United States Patent
Doddroe et al.

(10) Patent No.: US 6,863,695 B2
(45) Date of Patent: Mar. 8, 2005

(54) PROSTHETIC FOOT HAVING SHOCK ABSORPTION

(75) Inventors: Jeffrey L. Doddroe, Washington Court House, OH (US); Robert E. Arbogast, Mt. Sterling, OH (US); James M. Colvin, Hilliard, OH (US); James W. Capper, Mt. Sterling, OH (US); Sujatha Srinivasan, Columbus, OH (US)

(73) Assignee: Ohio Willow Wood Company, Mount Sterling, OH (US)

( * ) Notice: Subject to any disclaimer, the term of this patent is extended or adjusted under 35 U.S.C. 154(b) by 8 days.

(21) Appl. No.: 10/352,902

(22) Filed: Jan. 29, 2003

(65) Prior Publication Data

US 2003/0120354 A1 Jun. 26, 2003

Related U.S. Application Data

(63) Continuation of application No. 09/502,455, filed on Feb. 11, 2000.
(60) Provisional application No. 60/135,704, filed on May 24, 1999.

(51) Int. Cl.[7] .................................................. A61F 2/66
(52) U.S. Cl. ........................................................ 623/55
(58) Field of Search ............................ 623/55, 53, 54, 623/47, 48, 49, 52

(56) References Cited

U.S. PATENT DOCUMENTS

| | | |
|---|---|---|
| 3,754,286 A | 8/1973 | Ryan |
| 4,865,612 A | 9/1989 | Arbogast et al. |
| 5,116,384 A | 5/1992 | Wilson |
| 5,133,777 A | 7/1992 | Arbogast et al. |
| 5,258,039 A | 11/1993 | Goh et al. |
| 5,387,246 A * | 2/1995 | Phillips ........................ 623/56 |
| 5,458,656 A | 10/1995 | Phillips |
| 5,509,938 A | 4/1996 | Phillips |
| 5,549,711 A * | 8/1996 | Bryant ........................ 623/53 |
| 5,571,210 A | 11/1996 | Lindh |
| 5,653,767 A | 8/1997 | Allen et al. |
| 5,776,205 A * | 7/1998 | Phillips ........................ 623/55 |
| 5,800,563 A | 9/1998 | Arbogast et al. |
| 6,099,572 A | 8/2000 | Mosler et al. |
| 6,129,766 A | 10/2000 | Johnson et al. |

FOREIGN PATENT DOCUMENTS

| | | |
|---|---|---|
| EP | 0884033 | 12/1998 |
| FR | 484416 | 10/1917 |
| SU | 311635 | 8/1971 |
| WO | WO 9853769 | 12/1998 |

* cited by examiner

*Primary Examiner*—Bruce E Snow
(74) *Attorney, Agent, or Firm*—Oblon, Spivak, McClelland, Maier & Neustadt, P.C.

(57) ABSTRACT

A prosthetic foot includes an adapter element securable to a residual limb, a foot plate having a heel portion and a toe portion along the length thereof, at least one toe spring connected between the adapter element and the toe portion of the foot plate, and a heel spring connected between the adapter element and the heel portion. The heel spring may be a leaf spring or a tube type shock absorber. The concave side of the leaf spring exhibits a plurality of transverse ribs. Alternatively, a tubular pylon may have a collar mounted thereon for movement along the length of the pylon. A toe spring and a heel spring extend from the collar to form toe and heel portions of the prosthetic foot. A further heel spring is connected between the heel portion and another end of the pylon, and a non-extensible band extends between the heel portion and the collar. As another alternative, a tubular pylon has one end securable to a residual limb, and a collar is mounted to the pylon for movement along the length of the pylon. At least one toe spring is connected between the collar and the toe portion of a foot plate, while a heel spring is connected between the heel portion of the foot plate and another end of the pylon.

34 Claims, 6 Drawing Sheets

PROSTHETIC FOOT HAVING SHOCK ABSORPTION

The present application is based on Provisional Application Ser. No. 60/135,704, and is a continuation of patent application Ser. No. 09/502,455, filed Feb. 11, 2000.

BACKGROUND OF THE INVENTION

1. Field of the Invention

The invention is directed to a prosthetic foot which is able to absorb the shocks developed during ambulation with efficient energy transfer between heel strike and toe-off, and to enhance stability.

2. Description of the Related Art

Specialized prosthetic feet have recently been developed in an effort to satisfy the specialized needs of different amputees. For example, active amputees who engage in sports or other strenuous physical activities typically require a prosthetic foot which is capable of both absorbing energy during a heel strike of each step, of efficiently transferring the energy to the toe of the prosthesis as the step progresses, and of releasing the stored energy at the moment of toe-off to provide energy for the next step.

In particular, during ambulation the foot initially contacts the ground at the heel. During strenuous activities, it is desirable for a prosthesis to be able to absorb the shock of this heel strike, and to transfer the absorbed energy to the toe portion of the prosthetic foot for release upon the subsequent toe-off so that the rebound energy is maximized. An effort to design a prosthetic foot capable of storing and subsequently releasing energy during ambulation is disclosed in U.S. Pat. No. 5,458,656 in which the pylon is formed of two telescoping parts connected by a spring. An upper part of the pylon incorporates a top adapter for connection to the residual stump of the wearer while the bottom part supports heel and toe springs. The energy of a heel strike is absorbed by the spring during telescoping of the pylon and is intended to be released as the load is removed from the prosthesis during toe-off. However, this conventional design has a number of problems. The telescoping pylon tends to bind due to turning moments applied from the toe as the user's weight is shifted to the toe of the prosthesis. Since the telescoping pylon is designed to compress at heel strike while the toe spring is designed to flex between mid-stance and toe off, and the heel lever arm is much shorter than the toe lever arm, the stiffness of the telescoping pylon is typically less than the stiffness of the toe spring. For these reasons and because the toe spring is supported by the telescoping pylon, the pylon tends to remain compressed until after toe off, and so the energy of the heel strike is not efficiently transferred to the toe spring for use during toe-off. Since the toe spring and the telescoping pylon are acting in series when the toe is loaded, the telescoping pylon can dampen the energy return response of the toe spring, making the device less dynamic than desired. Also, since the toe portion of the prosthesis is mounted exclusively to the telescoping pylon, the height of the prosthesis may be excessive, and the apparent length of the user's leg will vary markedly during walking—an unnatural and undesirable tell-tale of the presence of the prosthesis.

SUMMARY OF THE INVENTION

It is an object of the present invention to provide a prosthetic foot which can absorb energy on heel strike and efficiently transfer the energy to the toe of the prosthesis for use during toe-off.

It is a further object of the invention to provide a prosthetic foot with enhanced stability, control, function and durability.

It is yet a further object of the invention to provide a prosthetic foot which is not subject to the shortcomings of the prior art.

According to a feature of the invention, a prosthetic foot includes an adapter element securable to a residual limb, a foot plate having a heel portion and a toe portion along the length thereof, at least one toe spring connected between the adapter element and the toe portion of the foot plate, and a heel spring connected between the adapter element and the heel portion.

Since the toe spring of the prosthetic foot according to this feature of the invention is connected between the foot plate and to the adapter element, it can efficiently transfer energy to the toe portion during toe-off.

According to a further feature of the invention, a prosthetic foot comprises an adapter element securable to a residual limb, a foot plate having a heel portion and a toe portion along the length thereof, and at least one toe spring connected between the adapter element and the toe portion of the foot plate, the toe spring comprising a curved leaf spring whose concave side exhibits a plurality of transverse ribs.

According to this feature of the invention, the transverse ribs create a more constant stress spring, and effectively distribute the bending stresses along the length of the spring. This minimizes the risk of delamination of the toe spring and permits more efficient energy transfer during toe-off.

According to yet a further feature of the invention, a prosthetic foot comprises a tubular pylon having one end securable to a residual limb, a collar mounted to the pylon for movement along the length of the pylon, a toe spring extending from the collar, a heel spring extending from the collar such that the toe and heel springs comprise toe and heel portions of the prosthetic foot, a further heel spring connected between the heel portion and another end of the pylon, and a non-extensible band extending between the heel portion and the collar.

The further heel spring according to this feature of the invention reduces loading at the socket of the prosthesis, and the non-extensible band limits the movement of the collar away from the heel during the rebound of the heel spring, and thereby promotes efficient energy transfer to the toe spring for release during toe-off.

According to yet a further feature of the invention, a prosthetic foot comprises a tubular pylon having one end securable to a residual limb, a foot plate having a heel portion and a toe portion along the length thereof, a collar mounted to the pylon for movement along the length of the pylon, at least one toe spring connected between the collar and the toe portion of the foot plate, and a heel spring connected between the heel portion and another end of the pylon.

According to yet a further feature of the invention, a prosthetic foot comprises elements made from layers of precured composite sheets bonded together with adhesives.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
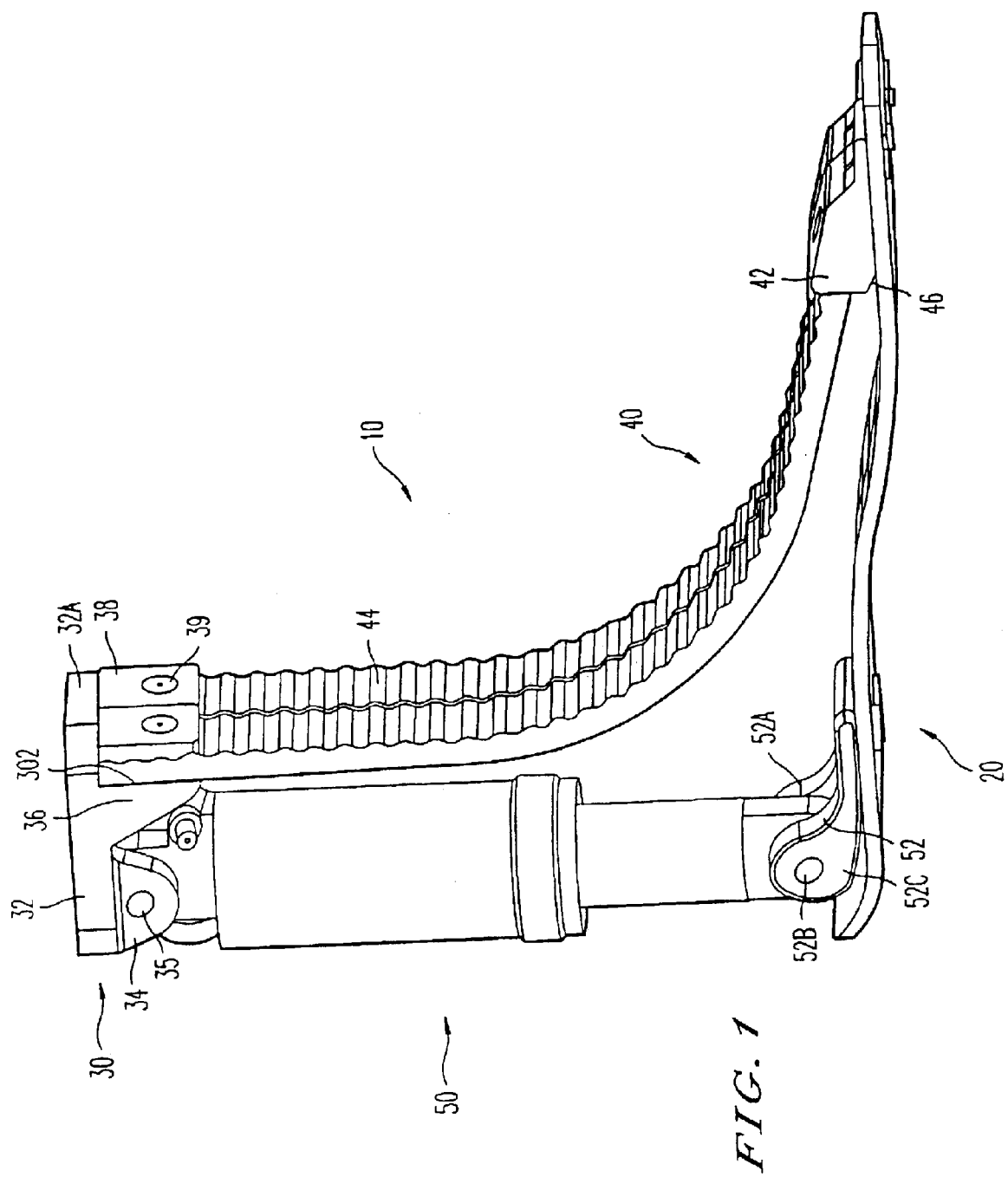
FIG. 1 is a front and side perspective view of a variant according to a first embodiment of a prosthetic foot of the invention.
Figure 2:
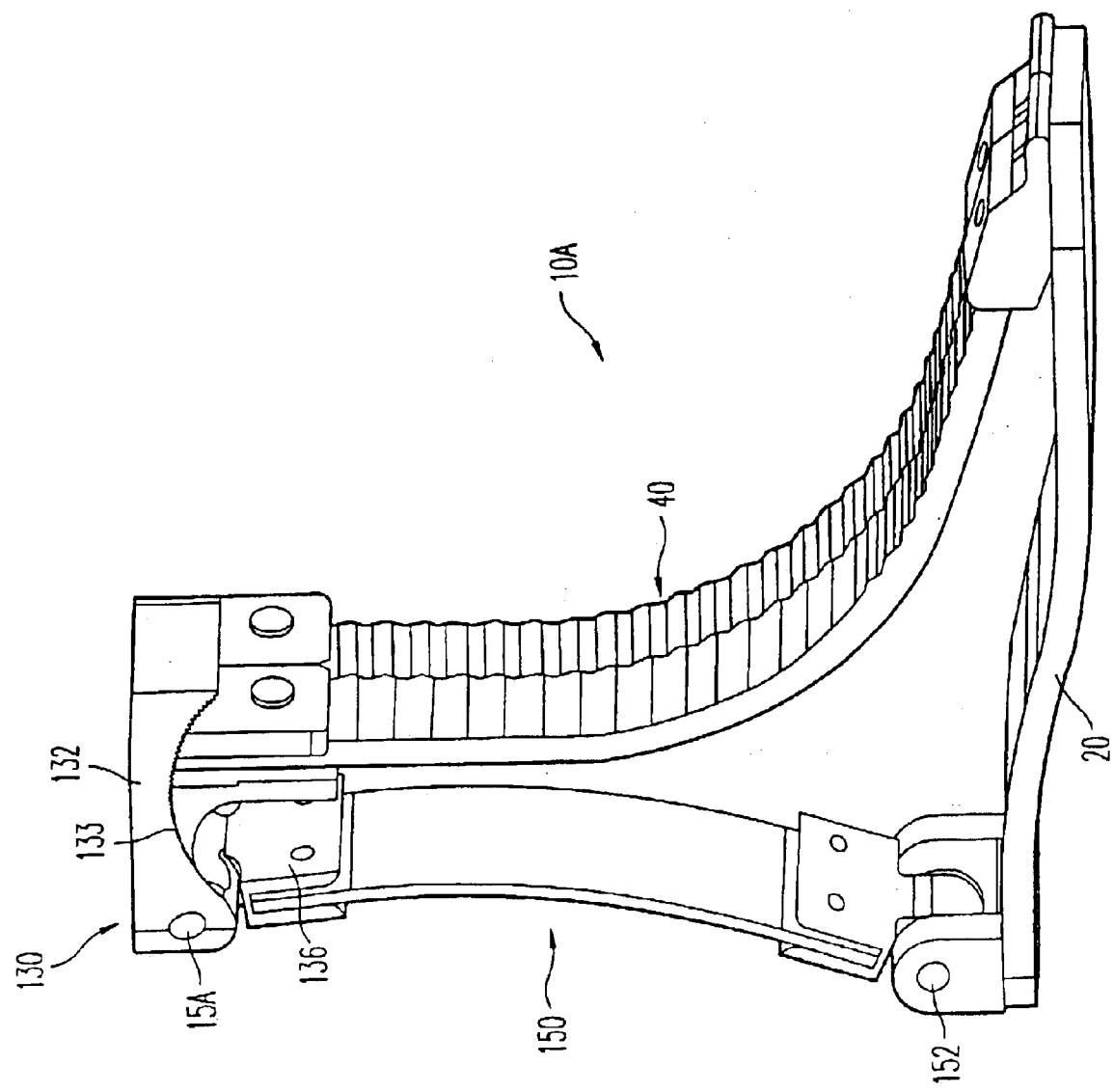
FIG. 2 is a front and side perspective view of a variation of the first embodiment of the prosthetic foot.

Referring now to the drawings wherein like reference numerals designate identical or corresponding parts throughout the several views, according to a first embodiment of the invention illustrated in the non-limiting FIGS. 1 and 2 of the drawings, and in particular the variant of FIG. 1, the main components of a prosthetic foot 10 comprise contoured foot plate 20, a top adapter 30, a pair of toe springs 40 and a heel spring/shock absorber 50.

Figure 1A:
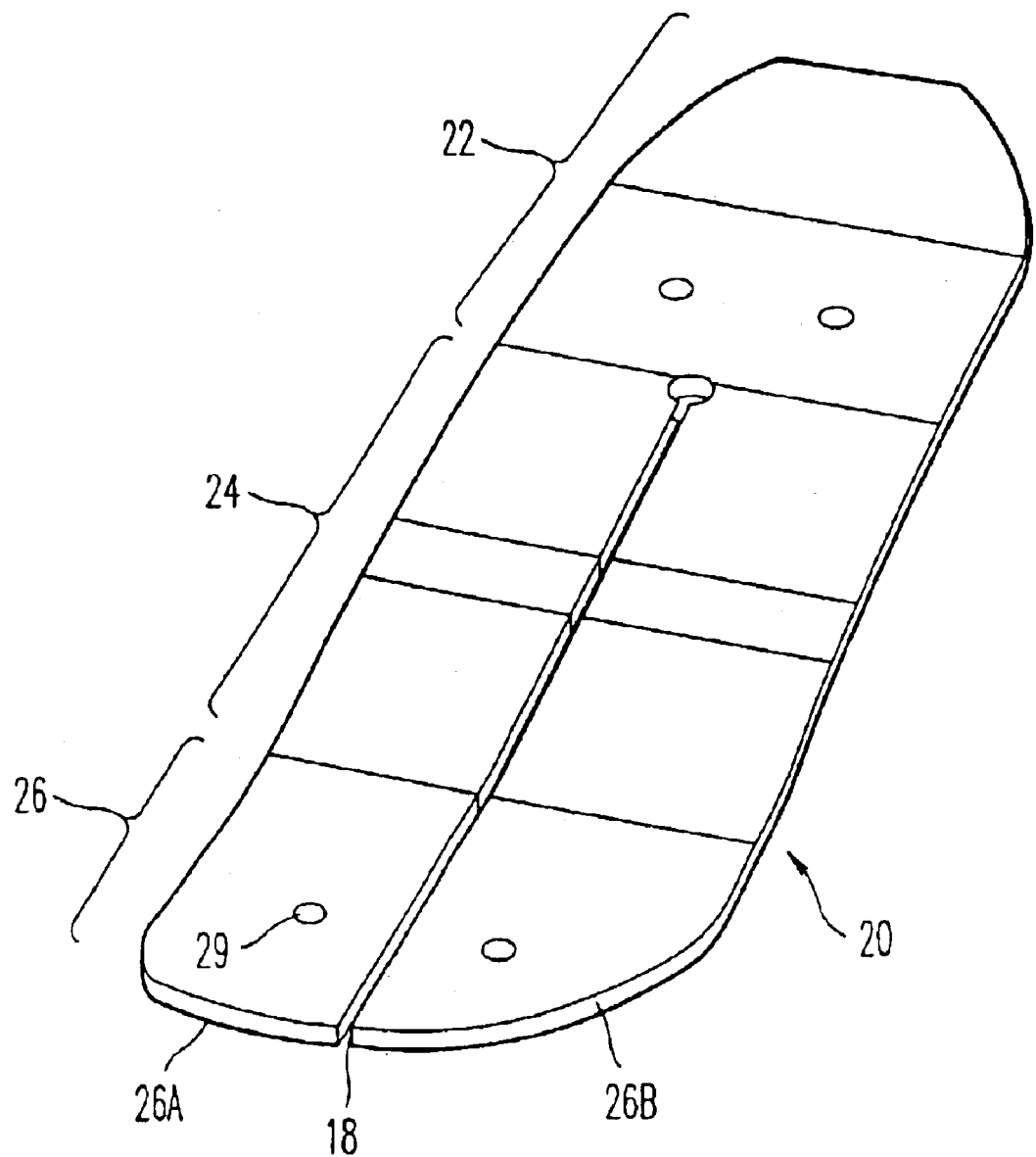
FIG. 1A is a top and side perspective view of a foot plate according to the invention.

The contoured foot plate 20 is generally conventional and could be that disclosed in U.S. Pat. No. 4,865,612, except as set forth below. It includes a heel portion 22, an arch portion 24 and a ball portion 26 (FIG. 1a). A slot 28 may extend through the foot plate and longitudinally from the toe portion to the heel portion for all or part of the length of the foot plate, and thereby divide the toe portion into separate left and right toe parts 26A and 26B.

The foot plate is formed of a composite material which may be continuous carbon fibers in an epoxy matrix. It has resilient, spring like qualities which permit it to deform during dorsi flexion and to resiliently rebound during toe-off to transfer energy to the next step. Preferably, the foot plate is formed from layers of precured composite sheets bonded together with adhesive. The foot plate may optionally have a shock absorbing pad on all or part of the distal surface. The foot plate may also optionally have a high friction material on all or part of the distal surface for use without a shoe or other foot covering.

The top adapter 30 is the interface that is used to attach the prosthetic foot to the remainder of the prosthesis, for example to a socket part or an angular alignment adaptor. It may use an industry standard four hole pattern or any other configuration for attaching the prosthetic foot to the remainder of the prosthesis via a tube clamp, a pyramid clamp, a bolt, or any other securement device. The angular alignment structure may also be built into the top adapter. Such alignments could include slide adjustment in the anterior/posterior direction; slide adjustment in the medial/lateral direction; axial rotation; dorsi flexion/plantar flexion rotation with adjustable heel height. In addition to such standard alignment components in the prosthetic industry, the top adapter could also include special or unique alignment elements without the need for additional fasteners. The top adaptor could also include elements to aid in the suspension of the prosthetic socket to the residual limb, such as a valve for suction suspension.

Figure 5:
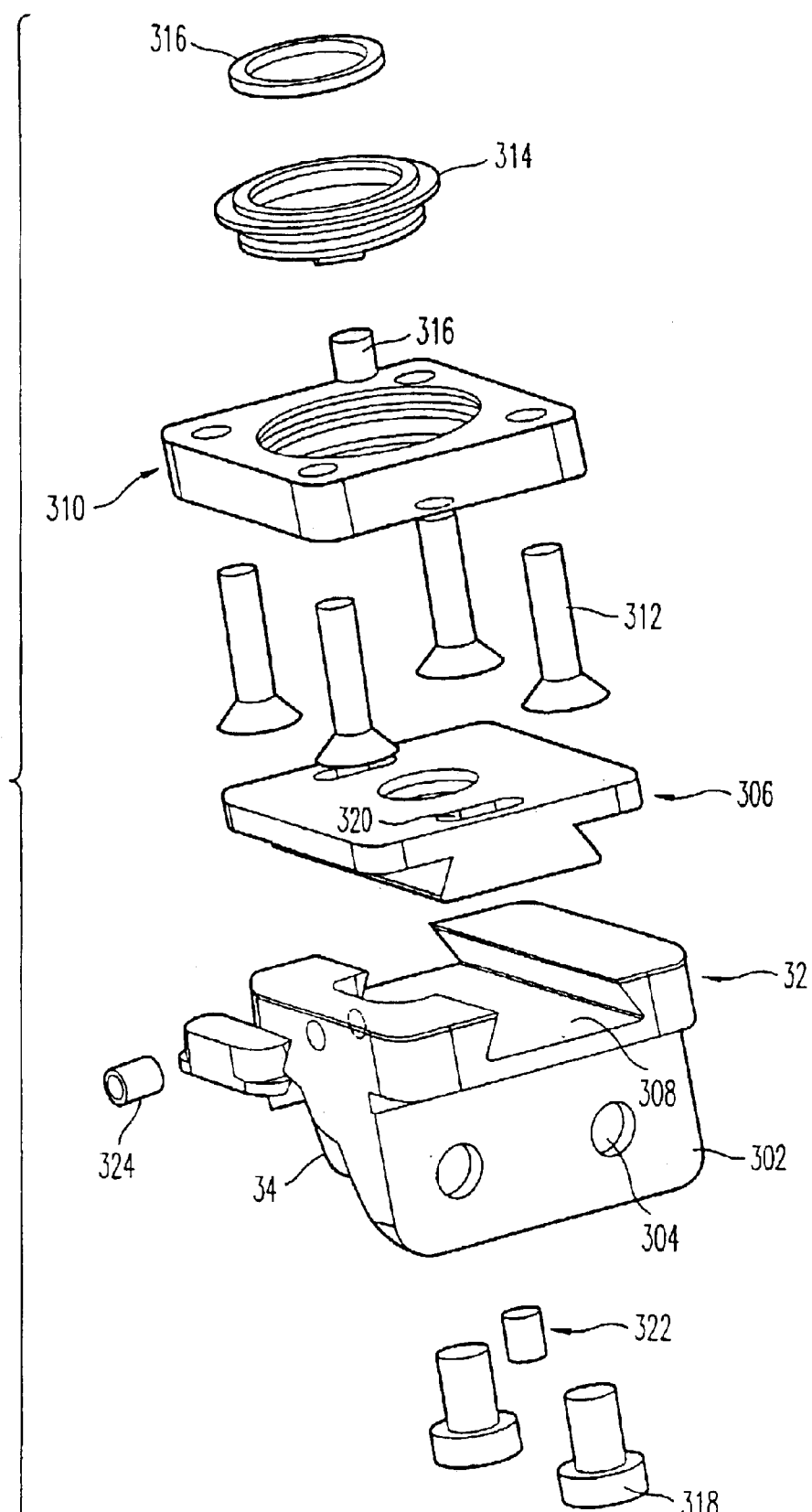
FIG. 5 is an exploded view of an example of a top adapter usable with the invention.

Referring particularly to FIGS. 1 and 5, the top adapter 30 preferably has a one piece cast, machined or molded top plate 32 such as a machined aluminum part including a pair of depending yokes 34 (only one is shown) via which the shock absorber 50 may be pivotally attached to the top adapter via a pair of journals 35 (only one is shown).

A downwardly directed integral shoulder 36 of the top plate 32 opposite the yokes 34 has a vertical front face 302 which provides a rear clamp support for the ends of the toe springs 40, which in the illustrated embodiment are clamped to the top adapter between the shoulder 36 and a pair of clamp plates 38. For example, screws or bolts 39 extending through the clamp plates and toe springs may be threaded into holes 304 of the shoulder 36 in order to rigidly clamp the ends of the toe springs 40 between the clamp plates 38 and the face of the shoulder 36.

A ledge 32A of the top plate extends forward of the shoulder 36 to provide an upper stop for the toe springs 40, to prevent upward movement of the compression side of the toe springs during deformation and to thereby reduce the possibility of shear failure of the toe springs in use. Also, although not illustrated in FIG. 1, the face of the shoulder 36 against which the toe springs are clamped may include serrations in order to better grip the toe springs. The clamp plates 38 may also have serrations which mate with the ribs (discussed below) of the toe springs 40. These serrations improve the clamping grip on the compression and tension sides of the toe springs to limit their relative movement during use and thereby reduce the risk of shear failure.

The top plate may be mounted to a stump socket via a dovetail slide and a rotatable adapter. For example, in this embodiment (FIG. 5) a dovetail slide member 306 has a dovetail portion which slides in a dovetail groove 308 of the top plate 32. A rotatable adaptor 310 may be screwed to a stump socket (not shown) by screws 312, and may optionally incorporate a check valve 314 and filter 316 to accommodate air expelled from the stump socket when it is mounted to a stump. The rotatable adapter 310 may be secured to the dovetail slide member 306, with rotation adjustment, by screws 318 which extend through curved slots 320 in the dovetail slide member 306, and are threaded into the rotatable adaptor 310. A slide limit screw 322 can be threaded into the top plate 32 to a position to interfere with, and limit, the movement of the slide member 306. The position of the dovetail slide member 306 in the dovetail groove 308 can be locked by tightening of a slide adjustment screw 324 threaded into the top plate 32.

Two, preferably identical, leaf springs 40 are each connected or clamped between the top adapter 30 and the toe of the foot plate 20. The clamping of one end of the toe springs to the top adapter has already been described. The opposite ends of the toe springs are similarly respectively clamped to the toe parts 26A and 26B of the foot plate 20. For example, a pair of toe spring clamps 42, which may be formed of machined aluminum, may each be bolted or riveted to a respective toe part 26A or 26B of the toe 26 of the foot plate, and may include clamp plates similar to clamp plates 38 for clamping the ends of the toe springs. To this end, the toe parts 26A and 26B may each include a hole 29 for the bolt or rivet of the clamp elements. Toe spring clamps 42 can provide or rigid or pivotal connection between toe springs 40 and toe part 26A or 26B of the toe 26 of the foot plate.

The toe spring clamps 42 are preferably shaped to form reliefs 46 at their posterior portions in order to allow the foot plate 20 to deflect around the toe spring clamps during heel strike. Optionally, they may also form anterior reliefs to allow the foot plate 20 to deflect around the toe spring clamps during toe-off. The toe spring clamps 42 maintain a spacing between the toe ends of the toe springs 40 and the foot plate so as to maximize the length of the toe springs available to deform during use. This, together with the clamping of the toe springs only at their ends, helps distribute the bending stresses along the entire length of the toe springs and reduces the possibility of failure.

The toe springs 40 themselves are each a leaf spring which is generally curved along its length to preferably have an unstressed arcuate end-to-end angle of 100 and 110°, with an overall spring radius of 3 to 3.5 inches. The toe springs 40 are each preferably formed by a laminate of two or more different composite materials. Each layer can preferably be formed of any combination of carbon/epoxy; glass/epoxy; glass/vinyl ester; or carbon/vinyl ester. Preferably, the tension (convex) side of the toe spring is formed of a layer using long fibers while the compression (concave) side of the toe spring is formed of a layer using short glass or other fibers. Also preferably, the toe springs are made of layers of precured composite sheets bonded together with adhesive. The toe springs could also be made from spring metal.

As an alternative the two toe springs may be replaced by a single toe spring which is split along its length from the toe end to near the end clamped by the top adaptor 30.

According to a feature of the invention, the surface of each of the toe springs 40 on the concave side exhibits a plurality of transverse ribs 44 for distributing bending stresses along the length of the toe springs. The toe springs normally have a tendency to bend disproportionately at a region near their longitudinal mid-portions. This results in high localized shear stresses which can produce delaminization of the layers of the toe spring. Addressing this problem by simply making the toe springs thicker is not a satisfactory solution because the toe springs will then be too stiff to provide the desired degree of compliance during ambulation.

The ribs 44 instead address this problem by locally altering the compliance of the ribs along their length. For example, larger radius ribs make the springs stiffer while a smaller radius provides less stiffness. Therefore by controlling, for example, the rib radiuses and spacing along the lengths of the springs, one can distribute the deformation of the spring during ambulation over the entire length of the spring, and thereby permit a greater overall deflection of the spring while minimizing localized shear stresses at any given portion along the spring length.

A typical rib radius may be 0.125 inches.

The shock absorber 50 is preferably a tube type shock absorber incorporating an air or hydraulic spring. For example, the "FLOAT" model bicycle shock absorber manufactured by Fox Racing Shox could be used as a shock absorber 50. The spring constant of this shock absorber can be adjusted by the user. One end of the shock absorber 50 is pivotally connected to the top adapter 30 via the journals 35 for rotation about an axis transverse to the length of the foot plate 20 and the length of the shock absorber. The other end of the shock absorber is pivotally connected to the foot plate 20 via a heel connector 52, for rotation about an axis transverse to the length of the foot plate 20 and the length of the shock absorber. To this end, the heel connector 52 also has yokes 52A and journals 52B. Alternatively, rotation in other planes could be achieved with the use of spherical bearings. The pivotal mounting of the shock absorber facilitates ankle rotation during walking, relieves stresses due to bending moments and minimizes the risk of binding of the shock absorber.

The heel connector can also include a posterior relief 52C to allow the foot plate to deflect around the heel connector during heel strike.

During ambulation, the shock absorber is compressed to absorb the shock of the initial heel strike for each step. The user can adjust the spring constant of the shock absorber to that required for the particular use. The pivotal mounting of the shock absorber minimizes turning moments and binding of the shock absorber. Also, since the prosthetic foot is mounted to the remainder of the prosthetic limb and the user's leg via the top adaptor 30, and not entirely via the shock absorber, any shortening of the prosthesis due to compression of the shock absorber at this time is minimized.

As the foot rotates from the heel strike towards toe-off during each step, the load is gradually transferred from the heel toward the toe of the foot plate 20, causing the foot plate to deform. This deformation of the foot plate 20 is resisted by the controlled bending deformation of the toe springs. A simultaneous elastic return of the shock absorber 50 also propels the user forward and transfers energy to the toe springs 40, causing them to further deform. The ribs 44 distribute the bending load along the length of the toe springs 40 and thereby minimize the risk of delamination or other spring failure. The shear stresses are also controlled by the tight grip of the toe springs provided by the serrations on the shoulder 25 and the clamp plates 38. The stop 32A also limits the differential movement of the compression sides of the toe springs, relative to the tension sides during bending, which also helps limit shear stresses.

The separate mounting of the toe springs 40 to the toe parts 26A and 26B permits the toe springs to individually respond to foot inversion or eversion.

Finally, during toe-off, the foot plate 20 and toe springs 40 rebound to provide energy transfer for the next step. Since the shock absorber 50 has fully returned by this time, a maximum energy transfer is possible.

The prosthetic foot of this design has several advantages over conventional prosthetic feet. The bonded layers of precured composite sheet construction of the toe spring, foot plate, and heel leaf spring increase durability by distributing stresses through the thickness of these elements. The ribbed construction of the toe springs increase their durability by distributing the shear stresses along the length of the toe springs. Since the shock absorber is in parallel with the toe spring and is pivotally connected, the shock absorber is not compressed at toe-off and so there is no damping of the toe spring energy return by the shock absorber. The generally triangular shape of the prosthesis provides a compact design, minimizes the limb shortening phenomenon and provides a smoother transition from heel to toe. The flexibility of the foot also facilitates "foot flat," i.e., broad surface area contact of the foot with the ground, which promotes stability. The generally triangular shape of the prosthesis can also increase durability by inherently restricting the maximum deflection of the flexible components. The air spring shock absorber provides a more dynamic response than currently available shock absorbers.

In the variant of FIG. 2, the prosthetic foot 10A is identical to that of FIG. 1, except as set forth below. In particular, the shock absorber 50 is replaced by a composite leaf spring 150 which is pivotally connected to both the foot plate 20 and the top adapter 130 by journals 152 and 154. The leaf spring 150 may also be ribbed in the same way as the toe springs 40. The leaf spring may be made of layers of precured composite sheets bonded together with adhesive. The leaf spring may be exchanged for another of different spring constant for different activities. Alternatively, composite leaf spring 150 could be replaced by any spring material such as metal or polymer, including urethane.

The variant of FIG. 2 may also use a modified top adapter 130 which incorporates a toe spring angle compensation mechanism, which is useful for compensating for different shoe heel heights. To this end, the part forming the shoulder 136 is not integral with the top plate 132. Rather, the top plate 132 has a concave arcuate serrated lower surface 133 to which a serrated top end of the shoulder part 136 may be clamped by a nut or other means. By selecting the point of clamping of the shoulder part 136 along the arcuate surface 133, one can adjust the attachment angle of the toe springs to the top adapter.

While the toe spring angle compensation mechanism is shown with respect to the variant of FIG. 2, it is equally applicable to that of FIG. 1. However, the design in FIG. 1 can also compensate for heel height adjustment (e.g., for different footwear) by adjusting fluid pressure in the shock absorber.

Figure 3:
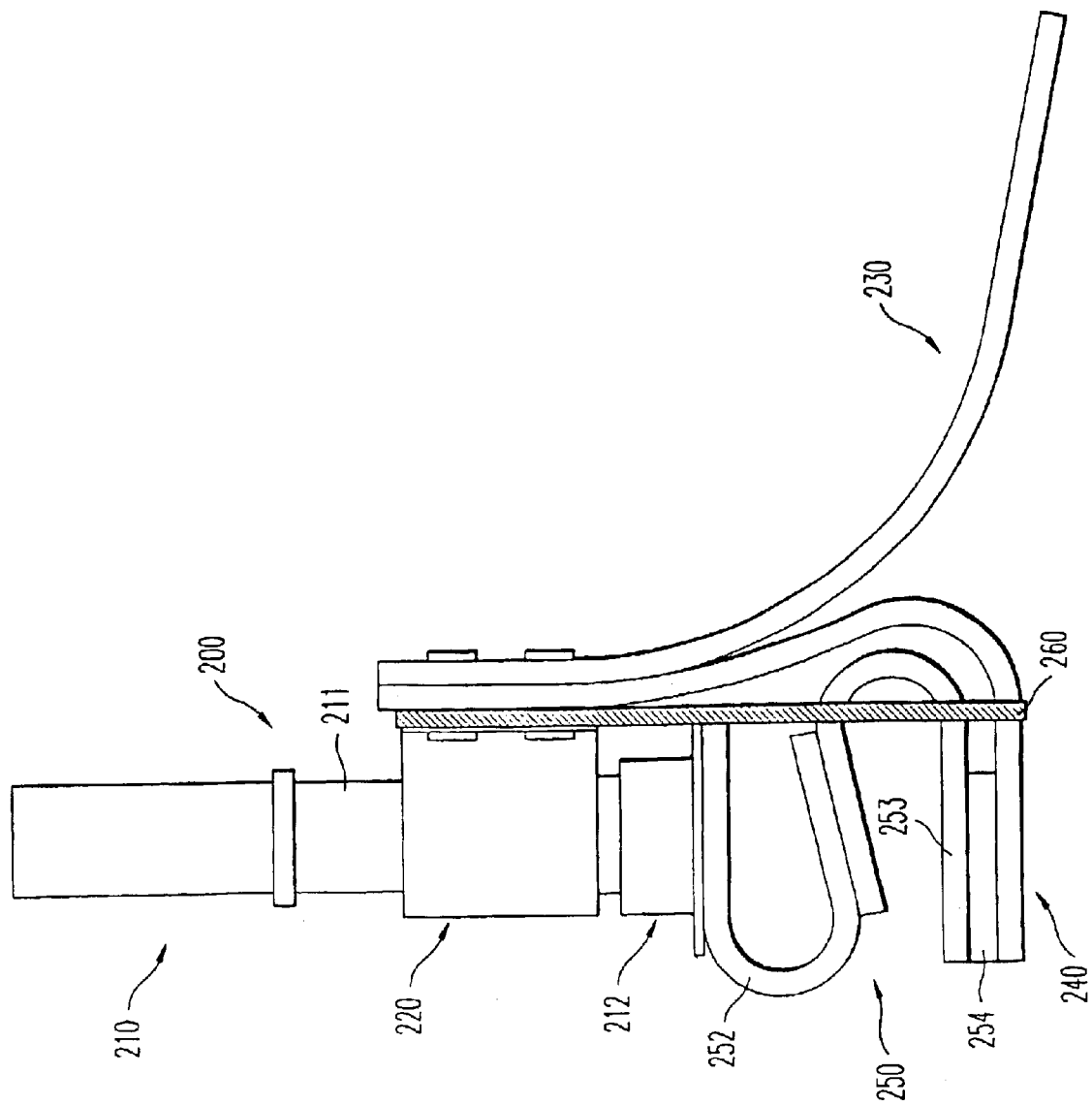
FIG. 3 is a side view of a second embodiment of a prosthetic foot according to the invention.

The main components of the prosthetic foot 200 according to the alternate embodiment of FIG. 3 include a pylon 210, a collar 220 slidably mounted to the pylon, a toe spring 230 forming a toe of the prosthetic foot, a heel spring 240 forming a heel of the prosthetic foot and a further, preferably S-shaped, heel spring 250 connected between the pylon 210 and the heel portion of the heel spring 230. Additionally, a band 260 made of a non-extensible material is wound around the heel spring and the collar 220 in order to limit the upward movement of the collar during the rebound of the further heel spring 250.

Turning more particularly to the specific embodiment illustrated in the figures, the pylon 210 may be a standard 30 mm tube having a top end connected to a socket in a conventional fashion. The collar 220 defines a bore (not illustrated) which closely surrounds the pylon such that the collar 220 can slide along the length of the pylon 210 without excessive friction or binding. To this end, the collar 220 is preferably made of machined aluminum, and either or both the surface of the pylon or the interior of the bore, in the area where the collar 220 reciprocates, can include a lining of low friction material as a linear bearing. For example, the pylon 210 may have a low friction material sleeve or sheathing 211.

The toe spring 230 and the heel spring 240 are fixed to the collar 220, for example by rivets or bolts. Bolts have the advantage that they permit adjustment of the position of fixation of the toe and heel springs onto the collar 220.

The toe spring 230 is preferably a composite leaf spring made from, e.g., glass or carbon fibers in an epoxy matrix. It is generally arcuate and forms the toe portion of the prosthetic foot. The heel spring 240 may be formed of the same material as the toe spring 230 and forms a heel portion of the prosthetic foot.

The further heel spring 250 is preferably S-shaped and may be formed from two C-shaped springs 252 and 253 which are bonded to one another, each of which may also be a composite spring of the same material as the toe spring 230. One end of the further spring 250 may be secured to lower end of the pylon 210, e.g., via tube clamp 212, while the other end of the further spring 250 may be fixed to the heel portion of the heel spring 240, for example by adhesively attaching the lower C-shaped spring 253 to a rubber bumper 254 which is itself adhered to the heel spring 240.

The non-extensible band 260 may be formed of Kevlar or of Spectra (a high molecular weight polyethylene manufactured by Allied Signal) loops.

During ambulation, the further heel spring 250 compresses during heel strike in order to absorb energy. When this occurs, the collar 220 is carried by the heel spring 240 and slides upwardly on the pylon 210. As foot rotation continues, the load is gradually transferred onto the toe spring 230 which is deformed thereby, and the further heel spring 250 simultaneously rebounds and transfers energy to the toe spring 230. As this occurs, the resulting load would normally cause the collar 230 to move to the top of the pylon 210, but this is prevented by the band 260.

The use of both the heel spring 240 and the further heel spring 250 provides a more natural feel and minimizes binding of the collar as it slides along the pylon.

The S-shape of the spring 250 prevents an angular change between the heel portion of the prosthetic foot and the pylon as the further heel spring 250 is compressed.

Figure 4:
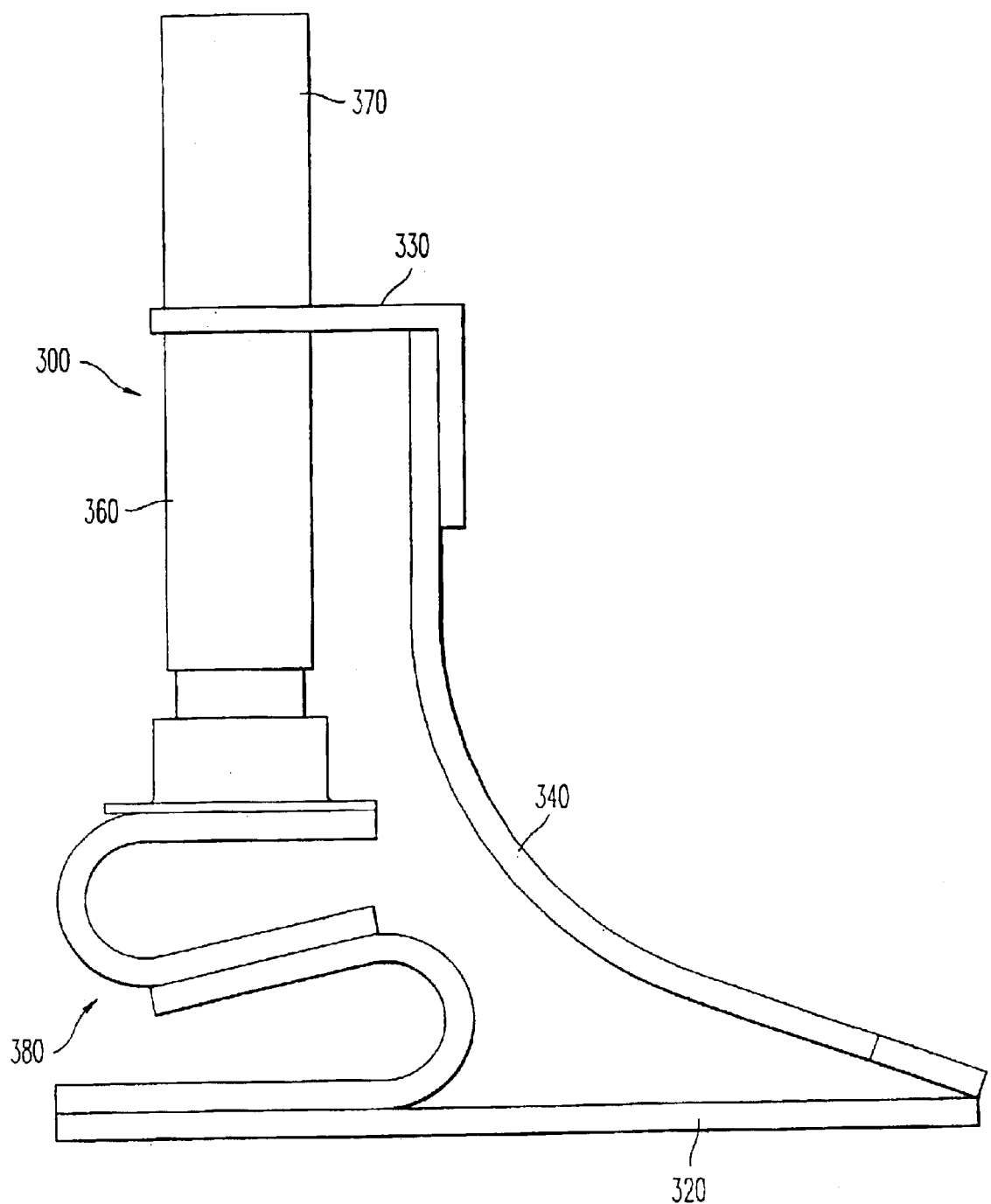
FIG. 4 is a schematic side view of a third embodiment of a prosthetic foot according to the invention.

The prosthetic foot 300 according to the further embodiment schematically illustrated in FIG. 4 represents a hybrid of the first two embodiments. In this embodiment, the foot plate 320 may be identical to that shown in FIG. 1 (although, for ease of illustration, its contouring is not shown). Similarly, the toe springs 340 may be identical to those of the first embodiment, and may be clamped in the same way (although this is also not shown).

According to this embodiment, the top adapter 330 incorporates a collar 360 similar to that of the second embodiment, and which slides along a pylon 370. A heel spring 380 may be S-shaped and correspond to the further heel spring of the previous embodiment. As in the previous embodiment, a non-extensible band (not shown) limits the upward movement of the collar 360.

Obviously, numerous modifications and variations of the present invention are possible in light of the above teachings. It is therefore to be understood that within the scope of the appended claims, the invention may be practiced otherwise than as specifically described herein.

What is claimed is:

1. A prosthetic foot comprising:
   an adaptor element securable to a residual limb;
   a foot plate having a heel portion and a toe portion spaced along the length thereof;
   a heel spring connected between said adaptor element and said heel portion;
   at least one toe spring connected between said adaptor element and said toe portion of said foot plate; and
   wherein at least one of the connection of the heel spring with the adaptor element and the connection of the heel spring with the heel portion of the foot plate is a pivotal connection having a pivot axis,
   wherein said foot plate is split at least at said toe portion to form first and second toe parts separated in a direction transverse to the length of the foot plate, and wherein said at least one toe spring comprises two toe springs, each of said two toe springs being secured to a different one of said first and second toe parts.

2. The prosthetic foot of claim 1, wherein said heel spring is a leaf spring.

3. The prosthetic foot of claim 2, wherein one end of said leaf spring is pivotally connected to said adaptor element, and wherein another end of said leaf spring is pivotally connected to said foot plate.

4. The prosthetic foot of claim 1, wherein said adaptor element, said foot plate, said at least one toe spring and said heel spring together form a generally triangular shape.

5. The prosthetic foot of claim 1, wherein said at least one toe spring comprises means for distributing bending stresses along the length of the at least one toe spring.

6. The prosthetic foot of claim 1, wherein said at least one toe spring is a concave leaf spring, and wherein a concave side of the at least one toe spring exhibits a plurality of transverse ribs.

7. The prosthetic foot of claim 6, wherein radii of said transverse ribs are set such as to distribute bending stresses along the length of the at least one toe spring.

8. The prosthetic foot of claim 1, wherein said at least one toe spring is a concave leaf spring, and wherein a material of the concave side of the at least one toe spring is different from the material of the convex side of the at least one toe spring.

9. The prosthetic foot of claim 1, wherein the at least one toe spring is formed of fiber reinforced plastic.

10. The prosthetic foot of claim 1, wherein opposite ends of said at least one toe spring are respectively clamped to said adaptor element and to said toe portion of said foot plate.

11. The prosthetic foot of claim 10, further comprising a toe spring clamp clamping said at least one toe spring to said toe portion of said foot plate, wherein said toe spring clamp and said toe portion define a posterior relief allowing the foot plate to deflect around the toe spring clamp.

12. The prosthetic foot of claim 1, further comprising a heel connector mounted to the heel portion of said foot plate and pivotally connected to an end of said heel spring, wherein said heel connector and said heel portion define a posterior relief allowing the foot plate to deflect around the heel connector.

13. The prosthetic foot of claim 1, wherein the resilient foot plate comprises at least two layers of precured composite sheets.

14. The prosthetic foot of claim 13, wherein the at least two layers of precured composite sheets are bonded together with an adhesive.

15. The prosthetic foot of claim 1, wherein the foot plate includes a shock absorbing pad on at least a portion of a distal surface of the foot plate.

16. The prosthetic foot of claim 1, wherein the at least one toe spring is resilient.

17. The prosthetic foot of claim 16, wherein the at least one resilient toe spring comprises at least two layers of precured composite sheets.

18. The prosthetic foot of claim 17, wherein the at least two layers of precured composite sheets are bonded together with an adhesive.

19. A prosthetic foot comprising:
an adaptor element securable to a residual limb;
a resilient foot plate having a heel portion and a toe portion spaced along the length thereof;
at least one toe spring connected between said adaptor element and said toe portion of said foot plate;
a heel spring connected between said adaptor element and said heel portion, wherein said heel spring affects vertical stiffness, wherein at least one of the connection of the heel spring with the adaptor element and the connection of the heel spring with the heel portion of the foot plate is a pivotal connection; and
a shock absorber connected between said adaptor element and said heel portion,
wherein said heel spring and said shock absorber are comprised by a tube shock absorber incorporating a fluid spring, and
wherein said fluid spring has a user adjustable spring constant.

20. The prosthetic foot of claim 19, wherein one end of said tube shock absorber is pivotally connected to said adaptor element and wherein another end of said tube shock absorber is pivotally connected to said foot plate.

21. The prosthetic foot of claim 19, wherein the resilient foot plate comprises at least two layers of precured composite sheets.

22. The prosthetic foot of claim 21, wherein the at least two layers of precured composite sheets are bonded together with an adhesive.

23. The prosthetic foot of claim 19, wherein the foot plate includes a shock absorbing pad on at least a portion of a distal surface of the foot plate.

24. The prosthetic foot of claim 19, wherein the at least one toe spring is resilient.

25. The prosthetic foot of claim 24, wherein the at least one resilient toe spring comprises at least two layers of precured composite sheets.

26. The prosthetic foot of claim 25, wherein the at least two layers of precured composite sheets are bonded together with an adhesive.

27. A prosthetic foot comprising:
an adaptor element securable to a residual limb;
a resilient foot plate having a heel portion and a toe portion spaced along the length thereof;
a heel spring connected between said adaptor element and said heel portion;
at least one toe spring connected between said adaptor element and said toe portion of said foot plate; and
wherein at least one of the connection of the heel spring with adaptor element and the connection of the heel spring with the heel portion of the foot plate is a pivotal connection having a pivot axis, wherein said foot plate is split at least at said toe portion to form first and second toe parts separated in a direction transverse to the length of the foot plate, and wherein said at least one toe spring is bifurcated to form two spring parts, each of said two toe spring parts being secured to a different one of said first and second toe parts.

28. A prosthetic foot comprising:
an adaptor element securable to a residual limb;
a foot plate having a heel portion and a toe portion spaced along the length thereof;
at least one toe spring connected between said adaptor element and said toe portion of said foot plate;
a heel spring connected between said adaptor element and said heel portion, wherein said heel spring affects vertical stiffness, wherein at least one of the connection of the heel spring with the adaptor element and the connection of the heel spring with the heel portion of the foot plate is a pivotal connection; and
a shock absorber connected between said adaptor element and said heel portion,
wherein said heel spring and said shock absorber are comprised by a tube shock absorber incorporating a fluid spring, and
wherein said fluid spring has a user adjustable spring constant.

29. A prosthetic foot comprising:
an adaptor element securable to a residual limb;
a foot plate having a heel portion and a toe portion spaced along the length thereof;
a heel spring connected between said adaptor element and said heel portion;
at least one toe spring connected between said adaptor element and said toe portion of said foot plate; and wherein at least one of the connection of the heel spring with adaptor element and the connection of the heel spring with the heel portion of the foot plate is a pivotal connection having a pivot axis, wherein said at least one toe spring is a concave leaf spring, and wherein a concave side of the at least one toe spring exhibits a plurality of transverse ribs.

30. The prosthetic foot of claim 29, wherein radii of said transverse ribs are set such as to distribute bending stresses along the length of the at least one toe spring.

31. A prosthetic foot comprising:

an adaptor element securable to a residual limb;

a foot plate having a heel portion and a toe portion spaced along the length thereof;

a heel spring connected between said adaptor element and said heel portion;

at least one toe spring connected between said adaptor element and said toe portion of said foot plate, wherein at least one of the connection of the heel spring with adaptor element and the connection of the heel spring with the heel portion of the foot plate is a pivotal connection having a pivot axis, and wherein opposite ends of said at least one toe spring are respectively clamped to said adaptor element and to said toe portion of said foot plate.

32. The prosthetic foot of claim 31, further comprising a toe spring clamp clamping said at least one toe spring to said toe portion of said foot plate, wherein said toe spring clamp and said toe portion define a posterior relief allowing the foot plate to deflect around the toe spring clamp.

33. A prosthetic foot comprising:

an adaptor element securable to a residual limb;

a resilient foot plate having a heel portion and a toe portion spaced along the length thereof;

a heel spring connected between said adaptor element and said heel portion; and at least one toe spring connected between said adaptor element and said toe portion of said foot plate, wherein at least one of the connection of the heel spring with adaptor element and the connection of the heel spring with the heel portion of the foot plate is a pivotal connection having a pivot axis, wherein opposite ends of said at least one toe spring are respectively clamped to said adaptor element and to said toe portion of said foot plate.

34. The prosthetic foot of claim 33, further comprising a toe spring clamp clamping said at least one toe spring to said toe portion of said foot plate, wherein said toe spring clamp and said toe portion define a posterior relief allowing the foot plate to deflect around the toe spring clamp.

* * * * *